(12) United States Patent
Lahue et al.

(10) Patent No.: US 6,489,115 B2
(45) Date of Patent: Dec. 3, 2002

(54) GENETIC ASSAYS FOR TRINUCLEOTIDE REPEAT MUTATIONS IN EUKARYOTIC CELLS

(75) Inventors: Robert S. Lahue, Elkhorn, NE (US); Juan J. Miret, South Grafton, MA (US); Richard Pelletier, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/742,025

(22) Filed: Dec. 21, 2000

(65) Prior Publication Data

US 2002/0119439 A1 Aug. 29, 2002

(51) Int. Cl.$^7$ .............................. C12Q 1/68; C12Q 1/02
(52) U.S. Cl. .............................................. 435/6; 435/29
(58) Field of Search ........................................ 435/6, 29

(56) References Cited

PUBLICATIONS

Juan Jose' PNAS et al, Orientation–dependent and sequence expansions of CTG/CAG trinucleotide repeats in *Saccharomyces cerevisiae*, vol. 95, pp. 12438–12443, Oct. 1998.*
Kremer, Berry et al., "A Worldwide Study of the Huntigton's Disease Mutation: The Sensitivity and Specificity of Measuring CAG Repeats." The New England Journal of Medicine. 330(20): 1401–1406 (1994).
Telenius, Hakan et al., "Somatic and gonadal mosaicism of the Huntington disease gene CAG repeat in brain and sperm." Nature Genetics. 6: 409–414 (1994).
Goldberg, Y. Paul, et al., "Molecular analysis of new mutations for Huntington's disease: intermediate alleles and sex of origin effects." Nature Genetics. 5: 174–179 (1993).
Campuzano, Victoria et al., "Friedreich's Ataxia: Autosomal Recessive Disease Caused by an Intronic GAA Triplet Repeat Expansion." Science. 271: 1423–1427 (1996).
Giovannucci, Edward, et al., "The CAG repeat within the androgen receptor gene and its relationship to prostate cancer." Proc. Natl. Acad. Sci. USA. 94: 3320–3323 (1997).
King, Bonnie L., et al., "Repeat Expansion Detection Analysis of (CAG)$_n$ Tracts in Tumor Cell Lines, Testicular Tumors, and Testicular Cancer Families." Cancer Research 57: 209–214 (1997).

Burright, Eric N., et al., "SCA1 Transgenic Mice: A Model for Neurodegeneration Caused by an Expanded CAG Trinucleotide Repeat." Cell. 82: 937–948 (1995).
Gourdon, Genevieve, et al., "Moderate intergenerational and somatic instability of a 55–CTG repeat in transgenic mice." Nature Genetics 15: 190–192 (1997).
Monckton, Darren G., et al., "Hypermutable myotonic dystrophy CTG repeats in transgenic mice." Nature Genetics 15: 193–196 (1997).
Mangiarini, Laura, et al., "Instability of highly expanded CAG repeats in mice transgenic for the Huntington's disease mutation." Nature Genetics 15: 197–200 (1997).
Graham, F. L., et al., "A New Technique for the Assay of Infectivity of Human Adenovirus 5 DNA." Virology 52: 456–467 (1973).
Hirt, Bernnard. "Selective Extraction of Polyoma DNA from Infected Mouse Cell Cultures." J. Mol. Biol. 26: 365–369 (1967).
Hsia, Han Chao, et al., "Comparison of Ultraviolet Irradiation–induced Mutagenesis of the lacI Gene in *Escherichia coli* and in Human 293 Cells." J. Mol. Biol. 205: 103–113 (1989).
Spiro, Craig, et al., "Inhibition of FEN–1 Processing by DNA Secondary Structure at Trinucleotide Repeats." Molecular Cell 4: 1079–1085 (1999).
Lieber, MR, et al., "Developmental stage specificity of the lymphoid V(D)J recombination activity." Genes & Development 1: 751–761 (1987).
Leeflang, Esther P., et al., "Analysis of germline mutation spectra at the Huntington's disease locus supports a mitotic mutation mechanism." Human Molecular Genetics 8(2): 173–183 (1999).
Boeke, Jef D., et al., "A positive selection for mutants lacking orotidine–5'–phosphate decarboxylase activity in yeast: 5–fluoro–orotic acid resistance." Mol Gen Genet 197: 345–346 (1984).

* cited by examiner

*Primary Examiner*—Terry McKelvey
(74) *Attorney, Agent, or Firm*—Dann, Dorfman, Herrell and Skillman

(57) ABSTRACT

A method for assaying trinucleotide repeat mutations in eukaryotic cells is provided.

22 Claims, 3 Drawing Sheets

GENETIC ASSAYS FOR TRINUCLEOTIDE REPEAT MUTATIONS IN EUKARYOTIC CELLS

Pursuant to 35 U.S.C. Section 202(c), it is acknowledged that the United States government has certain rights in the invention described herein, which was made in part with funds from the National Institutes of Health Grant No. GM61961.

FIELD OF THE INVENTION

The present invention relates to the fields of molecular biology and molecular genetics. More specifically, the invention relates to methods for identifying genetic alterations associated with cancer, Fragile X syndrome, Huntington's disease, myotonic dystrophy and other disorders.

BACKGROUND OF THE INVENTION

Several publications are referenced by numerals in parentheses in order to more fully describe the state of the art to which this invention pertains. Full citations for these references are found at the end of the specification. The disclosure of each of these publications is incorporated by reference herein.

Trinucleotide repeat (TNR) instability has recently been recognized as the mutational cause of at least 13 different inherited diseases (1–3). Increases in TNR lengths provide the molecular alterations associated with Huntington's disease (HD), Fragile X syndrome, myotonic dystrophy, SBMA (spinal and bulbar muscular atrophy), SCA I (spinocerebellar ataxia type I) and other syndromes.

Huntington's disease (HD) provides a paradigm of a genetic disease caused by TNR instability. HD is a progressive neurodegenerative malady that results in a number of symptoms, including choreic movement disorder and dementia (4). The disease typically first manifests itself in individuals in their 30's and 40's, and culminates in premature death 10–20 years later. The disease is inherited in an autosomal dominant manner, with particularly severe effects when inherited from the father.

The genetic phenomenon known as anticipation has also been associated with TNR diseases, including HD. Anticipation is found when the disease presents more severely or occurs with earlier onset with each generation. This non-Mendelian inheritance pattern was puzzling for many years. It has now been elucidated by molecular analysis of the mutated loci.

It is now accepted that the vast majority of TNR disease cases result from the expansion of naturally occurring TNR's. The HD gene, for example, contains a series of CAG's within the coding region of the corresponding protein, huntingtin (4). This repeat tract of CAG codons encoding glutamine residues, normally occurs 10–29 times in unaffected populations. However, 36–121 copies have been observed in patients afflicted with HD (4,5). The correlation between TNR length and the disease state is extremely high (>95%), lending strong support to the hypothesis that this mutation is intimately linked to the disease (4,5). The correlation between TNR length and HD has been verified using a transgenic mouse model for HD (6) in which a transgene containing the expanded CAG tract was sufficient to induce symptoms in mice similar to those observed in HD.

Examination of human families with a history of HD indicates that increases in TNR's occur both in the germline and in somatic tissue (4,5,7). Gains in TNR length can be quite large, even between successive generations, especially in cases where the parent harbors 30–35 repeats, a number that is intermediate between normal and diseased states (8).

As mentioned previously, TNR instability is now known to be a causative factor in at least 12 other genetic diseases (1–3). In each case, a distinct gene containing a TNR has increased in length in diseased individuals. The triplet sequences known to undergo TNR expansions are CNG (where N is any nucleotide) or GAA(9).

Instability appears to be restricted to these repeats, as there is no evidence to date to suggest instability of other triplet sequences, such as TAG or GAC. A number of molecular characteristics varies with each disease. For example, the TNR tract can reside within or outside of a structural gene. The number of repeats in the diseased versus normal populations varies widely between diseases. For example, this number can be in excess of 2,000 repeats for myotonic dystrophy (10). The mutant gene is expressed in some diseases but not in others. The encoded proteins have widely different biochemical properties. Additionally, the pattern of germline and somatic variation differs.

In addition to genetic disorders, emerging evidence supports an important connection between TNR instability and prostate and testicular cancer. In prostate cancer, TNR length affects cancer risk (11) due to the presence of an unstable CAG repeat in the androgen receptor (AR) gene (12). Deletions of the CAG tract are sometimes associated with prostate tumor formation (13). A molecular explanation for these findings is provided by mutational studies (14) that have shown AR transactivation of important AR-responsive genes is directly related to the number of CAG repeats. Clearly AR function depends on TNR length and hence is directly affected by the genetic stability (or instability) of the tract. For testicular cancer, expansion of CAG tracts was observed in five different families predisposed to this malignancy (15). That study concluded that CAG expansion may play an important role in testicular tumorigenesis. However, the gene or genes responsible for CAG instability in prostate and testicular tumor cells have not yet been identified.

Given the medical importance of TNR mutations and the novel genetic behavior of these elements, intense efforts are underway to elucidate the mechanism (or mechanisms) underlying TNR instability in human cells. However, to date there are at least three major experimental limitations which have hampered progress of these efforts. First, nearly all investigations have been limited to tissue samples from affected human kindreds. Second, analysis has typically been confined to endogenous (naturally occurring) DNA sequences, as opposed to test sequences that are more easily manipulated. Third, it has been difficult, if not impossible to identify individual cells which have undergone expansions. Instead, physical methods such as PCR or Southern blotting have been performed on unselected cell populations.

To further confound analysis, transgenic mice strains have been established that harbor human TNR-containing genes but do not appear to have large, frequent TNR expansions. Surprisingly, the TNR sequences in transgenic mice are very stable (16–19). In these studies, parts or all of human genes (HD, SCA I, etc.) that include CAG/CTG tracts of 55–162 repeats were integrated into the mouse genome at the corresponding loci. The genetic stability of these sequences was monitored both in somatic tissue and through intergenerational transmission. The TNRs in these transgenes show no alterations (11) or small changes of 1–8 repeats in tract size (17–19). Approximately equal numbers of expansions and contractions have been observed. Perhaps TNR expansions appear at higher rates in humans due to some aberrant DNA metabolic event that is absent in mice. These results serve to underscore the importance of using human cells for studies on the stability of TNRs.

SUMMARY OF THE INVENTION

In accordance with the present invention, methods are provided for the rapid and efficient analysis of trinucleotide repeat (TNR) tract alterations in mammalian cells. An exemplary method of the invention entails contacting mammalian cells with a shuttle vector under conditions whereby the shuttle vector enters the cells and replicates therein. Following replication, the shuttle vector is recovered and transfected into yeast cells under selection pressure. Alterations of the TNR tract in the mammalian cell results in a restoration of histidine or uracil expression for example, from the shuttle vector, thereby allowing the transfected yeast cells to survive in the absence of these agents. Only those yeast cells containing altered TNR tract lengths survive in the presence of the selection agent. The shuttle vector DNA may optionally be isolated. Alteration in TNR tract length DNA is then characterized using conventional molecular biology techniques. Such methods include, without limitation, polymerase chain reaction, nucleotide sequencing and gel electrophoresis. The shuttle vector DNA comprises TNR tracts having trinucleotides selected from the group consisting of CAG, CTG, CCG, CGG, GAA, TAG, and "scrambled" C,T,G. In a preferred embodiment, the TNR tract DNA is operably linked to a reporter molecule. An exemplary shuttle vector of the invention further comprises an SV40 origin of replication, a yeast HIS3 gene, yeast autonomous replication sequence elements, a centromere element, an *E. coli* origin of replication and at least one nucleotide sequence encoding a selectable marker.

In a further embodiment of the invention, the shuttle vector DNA contains a TNR tract isolated from a trinucleotide repeat instability gene selected from the group consisting of FMR1, FMR2, X25, DMPK, SCA8, SCA12, AR, HD, DRPLA, SCA1, SCA2, SCA3, SCA6 and SCA7. Optionally, the shuttle vector further comprises between 5 and 200 flanking nucleotides from said trinucleotide repeat instability gene.

In a preferred embodiment of the invention, a method for identifying TNR tract expansions is provided. An exemplary method for assaying TNR tract expansions entails contacting mammalian cells with a shuttle vector containing a TNR tract length of approximately 25 repeats under conditions whereby the shuttle vector enters the cells and replicates therein. Following replication, the shuttle vector is recovered and transfected into yeast cells under selection pressure. Alterations of the TNR tract in the mammalian cell results in a restoration of histidine expression from the shuttle vector, thereby allowing the transfected yeast cells to survive in the absence of histidine. Yeast cells containing expanded TNRs are selected and the shuttle vector DNA is isolated.

In yet another preferred embodiment of the invention a method for identifying contractions in TNR tract lengths is provided. An exemplary method for assaying contractions in TNR tract lengths entails contacting mammalian cells with a shuttle vector containing a TNR tract length ranging from 33 to 50 repeats under conditions whereby the shuttle vector enters the cells and replicates therein. Following replication, the shuttle vector is recovered and transfected into yeast cells under selection pressure. Contractions of the TNR tract in the mammalian cell results in a restoration of uracil expression from the shuttle vector, thereby allowing the transfected yeast cells to survive in the absence of uracil. Yeast cells containing contracted TNR tract lengths are then selected and the shuttle vector DNA is isolated.

The methods described herein will facilitate the identification and characterization of the molecular mechanisms and components involved in trinucleotide tract instability disorders.

DETAILED DESCRIPTION OF THE INVENTION

Figure 1:
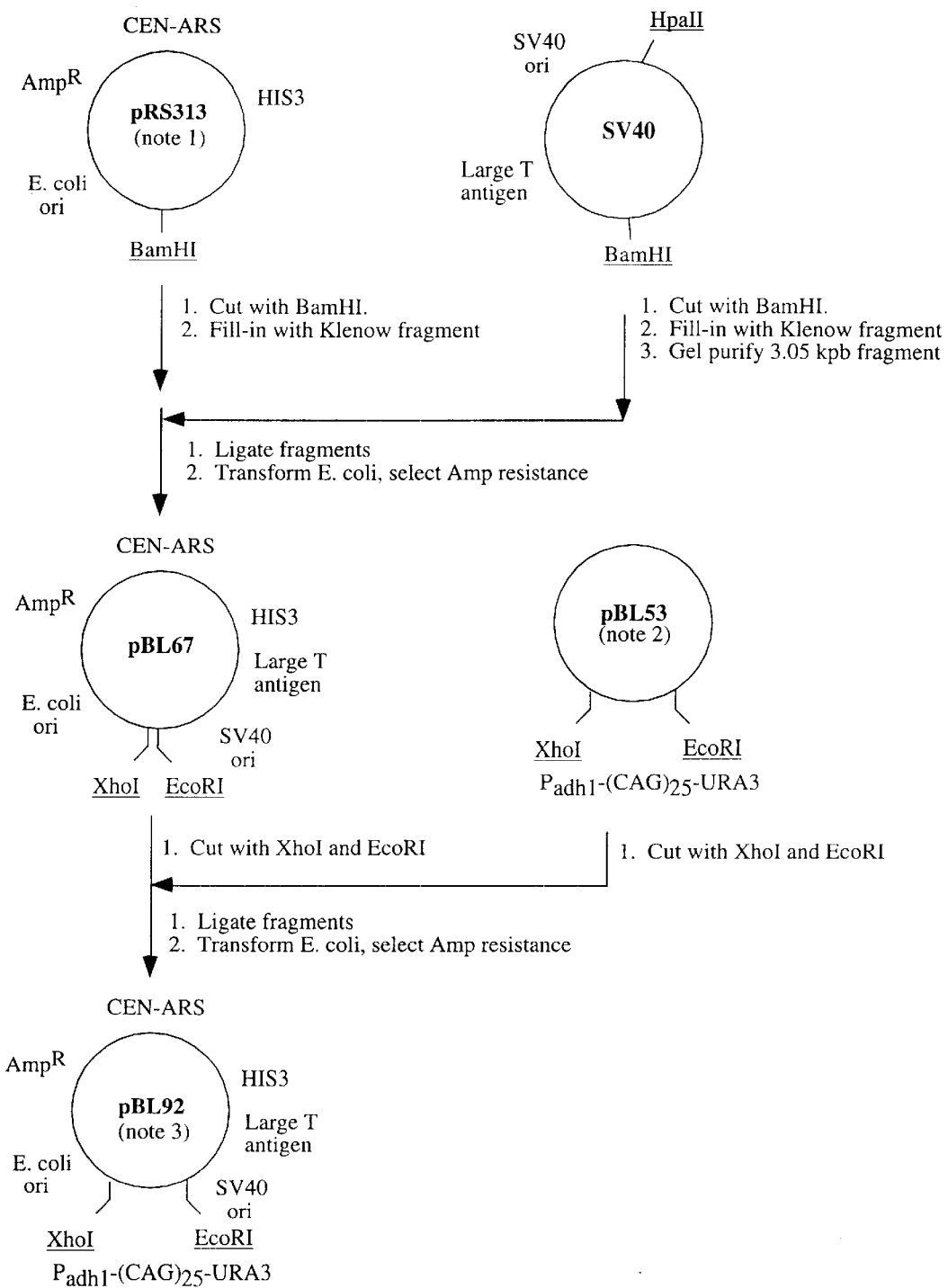
FIG. 1 shows a schematic diagram of the protocol used to prepare the shuttle vectors of the invention.

Mutations within trinucleotide repeats (TNRs) have recently been recognized as genetic alterations that contribute to human disease and cancer. A number of TNR-containing loci are genetically unstable, frequently giving rise to expansions (increases in tract length) or contractions (decreases in length).

Progress in elucidating the molecular mechanism (or mechanisms) of TNR instability in humans has been limited by the lack of a genetic assay for TNR mutations. Most research to date has been restricted to observational studies of TNR mutations in tissue biopsies or cell samples from affected kindreds. Physical techniques are used to identify TNR alterations. These techniques include Southern blots, restriction digests, polymerase chain reaction (PCR) and/or DNA sequencing. However, most of the techniques currently in use are non-selective. That is, these techniques do not directly select for human cells with TNR of altered lengths. To overcome this limitation, an experimentally tractable system to investigate TNR mutability in human cell culture has been developed by the present inventors.

The TNR assay provided herein may be used to advantage to identify and quantitate TNR mutations which occur by expansions or contractions of the TNR repeat tracts in human cells. This method facilitates selection of cells harboring expanded or contracted alleles which are then identified genetically. The assay also facilitates quantitation of mutation rates in the selected cells.

In addition, compounds or cellular components that regulate alterations in TNR length may be screened using the assay of the invention. Cell lines that are deficient in known DNA metabolic pathways, such as repair or recombination, may also be examined to assess the role these processes play in TNR instability. MEFs (mouse embryo fibroblasts) or ES (embryonic stem) cells from gene-specific knockout lines provide suitable cellular based starting materials for assessing the role of known genes in TNR instability. Cell lines which may be examined using the assay of the invention include: (1) cell lines defective in mismatch repair such as MSH2-/-, MLH1-/- and PMS2-/-; (2) cell lines defective in nucleotide excision repair such as ERCC1-/- and ERCC2-/-;

(3) cell lines defective in double-strand break repair such as RAD51-/-, XRCC1-/-, MRE11-/-; and (4) cell lines defective in non-homologous end joining such as Ku70-/-, Ku80-/- and DNAPK-/-.

Different TNR alleles may also be used to advantage to assess alteration patterns in human cells. Such alleles include interrupted or imperfect TNRs which expand at much lower frequencies in human cells and in yeast cells than perfect TNR tracts. In an additional aspect, the TNR mutability constructs of the invention may be used in methods for transferring TNR DNA between predetermined host cells including, for example, human, yeast, mammalian, bacteria and insect cells.

I. Definitions

The following definitions are provided to facilitate the understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of a nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

A "shuttle vector" is a vector which contains the appropriate control elements for expression in a plurality of cell types.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon, such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

A "clone" or "clonal cell population" is a population of cells derived from a single cell or common ancestor by mitosis.

A "cell line" is a clone of a primary cell or cell population that is capable of stable growth in vitro for many generations.

A "trinucleotide repeat" (TNR) is a tandemly repeated simple sequence typically arranged in tracts of three (3) nucleotides per repeating unit.

A "scrambled C,T,G" is a trinucleotide repeat tract containing a randomized sequence of C's, T's, and G's, i.e., a trinucleotide repeat that is not associated with a disease state or the target of TNR alterations.

II. Shuttle Vectors and Methods of Use Thereof

DNA encoding any sequences which undergo TNR alterations may be utilized in the shuttle vectors of the invention. Such TNR sequences include without limitation CGG, CTG and CAG. Table I summarizes the Genbank Accession numbers for the specific genes affected by TNR's in these disorders and provides the location of the TNR tracts within the affected genes.

TABLE I

GENBANK ACCESSION NUMBERS AND LOCATION WITHIN AFFECTED GENES WHERE TNR'S OCCUR IN GENETIC DISORDERS CAUSED BY TNR'S

| Disease Nucleotide #'s | $(TNR)_n$ | Gene | Accession # | Repeat |
|---|---|---|---|---|
| Fragile X syndrome | CGG | FMR1 | AC016925 | 14691–14744 |
| Fragile XE syndrome | CGG | FMR2 | AF012603 | 21–65 |
| Friedreich's ataxia | GAA | X25 | U43478 | 2185–2212 |
| Myotonic dystrophy | CTG | DMPK | NM004409 | 2890–2922 |
| [1]SCA8 | CTG | SCA8 | AF126749 | 1112–1348 |
| SCA12 | CTG | SCA12 | AF152102 | 2088–2366 |
| [2]SBMA/Kennedy's disease | CAG | AR | NM000044 | 1286–1345 |
| Huntington's disease | CAG | HD | NM002111 | 367–435 |
| [3]DRPLA/Haw River syndrome | CAG | DRPLA | NM001940 | 1673–1715 |
| SCA1 | CAG | SCA1 | NM000332 | 1524–1613 |
| SCA2 | CAG | SCA2 | NM002973 | 658–723 |
| SCA3/Machado-Joseph disease | CAG | SCA3 | NM004993 | 931–972 |
| SCA6 | CAG | SCA6 | AB035726 | 6975–7046 |
| SCA7 | CAG | SCA7 | NM000333 | 649–678 |

[1]SCA8 = spinocerebellar ataxia type 8. Other SCA syndromes are denoted analogously.
[2]SBMA = Spinobulbar muscular atrophy.
[3]DRPLA = Dentatorubral-pallidoluysian atrophy.

In one embodiment, the TNR sequences found in the disorders listed-above may be inserted into the shuttle vectors of the invention to measure TNR mutability. In a preferred embodiment, TNR tract lengths of about 25 repeats will be inserted into the shuttle vectors for TNR expansion assays, and TNR tract lengths of approximately 33 or 50 repeats will be inserted into the shuttle vectors for TNR contraction assays. In an alternative embodiment of the invention, native DNA flanking either side of the TNR tracts isolated from within the affected genes may be inserted along with the TNR tracts in the shuttle vectors. Up to 200 nucleotides on either side of the TNR tracts may be included. Lastly, these TNR sequences may also be inserted into a replicable vector for further cloning or for expression of a gene product.

There are many suitable vectors available for use in the assays of the invention. Most expression vectors are "shuttle vectors", i.e., they are capable of replication in at least one class of organism, and may then be transfected into another class of organism for expression. For example, a vector that was cloned in E. coli may subsequently be transfected into yeast or mammalian cells for expression.

Each replicable vector contains various sequence elements to facilitate expression of replication in the selected host organism. Replicable cloning and expression vector sequence elements include without limitation, a signal sequence, an origin of replication, one or more selectable marker genes, an enhancer element, a promoter and a transcription termination sequence.

An exemplary vector of the invention includes a TNR operably linked to a URA3 marker gene. The vector also comprises an SV40 origin of replication, as well as the sequence encoding the SV40 large T antigen to facilitate replication of the vector in 293T cells. The vector also contains an E. coli origin of replication, an ampicillin resistance gene, as well as an autonomously replicating yeast sequence element operably linked to a HIS3 selectable marker gene.

The following examples provide an illustrative method of practicing the instant invention and are not intended to limit the scope of the invention in any way.

EXAMPLE 1

TNR Expansions in Eukaryotic Cells

The mechanisms underlying TNR instability are of great interest because of the observed association with genetic disease. However, the investigation of TNR instability in human cells has been hindered because experimental systems currently in place fail to analyze TNR alterations in a step-wise fashion. The present invention provides a new procedure which overcomes this limitation and establishes an experimentally malleable system which can be used to investigate TNR mutability in human cell culture.

The present invention combines the convenience of tissue culture cells with the power of yeast genetics as a new approach for understanding TNR instability. This approach involves transfecting a DNA plasmid into cultured human cells, allowing expansions to occur during replication in those cells, and then rescuing the plasmid DNA and transforming it into yeast. Only those yeast cells that take up a plasmid with an altered TNR tract survive under selection pressure.

The assay of the invention is sensitive and quantitative. The protocol is also experimentally malleable. The shuttle vector (discussed below) is designed to permit testing of different TNR sequences in many different cell systems. In one embodiment of the present invention, TNR alteration is assessed in 293T cells transfected with the shuttle vector. In further embodiments, LoVo cells, HCT116 cells, DLD1 cells, XP-A cells, XP-B cells, cancer cells, normal primary cells, neuronal cells, tumor cells, muscle cells, hepatocytes, myocytes, fibroblasts or cells from individuals afflicted with a TNR-associated disorder may be used to assay for TNR instability. Additionally, this approach allows for PCR amplification and analysis of the altered tracts in order to determine the precise size of the alterations.

I. Materials and Methods

The following protocols are provided to facilitate the practice of the present invention.

Tissue culture protocols:

Human 293T cells (a human embryonic kidney cell line) were cultured in Dulbecco's minimal Essential medium (DMEM) supplemented with 10% fetal bovine serum, 50 units/ml penicillin-streptomycin (Gibco BRL) and 1X anti-PPLO agent (Gibco BRL). For the transfection experiments, supercoiled DNA (10 to 15 $\mu$g) was used to transfect exponentially growing 293T cells (1.5×106 cells per 175 cm$^2$ flask) by the calcium phosphate coprecipitation method (20). After 2–3 days of growth at 370C, the cells were lysed with 1.0–1.5 ml of Hirt's lysis buffer (21), and the lysate was pooled into a test tube (1.5 ml). NaCl 5M was added to each lysate (125 ml per 500 ml of lysate), and stored overnight at 4° C. The lysate was then spun for 15 minutes at 4° C. in a microcentrifuge. The supernatant, containing the plasmid DNA, was collected into a fresh tube. To remove proteins, the lysate was extracted twice with an equal volume of phenol/chloroform, and once with chloroform alone. The DNA was then precipitated with two volumes of ethanol, and resuspended in 100 $\mu$l TE (pH 7.5).

Plasmid preparation protocols:

Each plasmid DNA was prepared from E. coli by the alkaline lysis method and purified by two successive rounds of CsCl centrifugation (22), or by the Qiagen method (plasmid maxi-kit, Qiagen Inc.). FIG. 1 depicts a schematic diagram of the protocol used for preparing an exemplary shuttle vector of the invention.

DpnI digestions and yeast protocols:

For DpnI resistance assays, 50 $\mu$l of the plasmid DNA was digested for 1–2 hours with an excess of DpnI (New England Biolabs) enzyme (approx. 40 units) in approximately 60 $\mu$l of the buffer provided by the manufacturer. A fraction of the digest was used to transform yeast W303 cells (MATa leu2-3,112 trp1-1 ura3-1 can1-100 ade2-1 his3-11,13). A fraction of each transformation mixture (typically $\frac{1}{200}^{th}$) was then plated onto SC-His plates (synthetic complete, lacking histidine), and the remainder onto selective media: SC-His+5FOA (to score for expansions) or SC-His-Ura (to score for contractions). Colonies on each plate were counted after 2–3 days of growth at 30° C. The frequency of expansion (or contraction) was determined by the number of colonies obtained on selective media divided by the number of colonies found on SC-His plates (total number of transformants).

Background level, defined as the frequency of plasmid molecules that had incurred a mutation either during propagation into E. coli, or during replication in yeast cells, was determined as follows: Plasmid DNA (up to 5 $\mu$g) prepared from bacteria, was used to transform yeast as described above. A fraction of the transformation mixture was plated onto Sc-His plates (total transformants) and the remainder onto SC-His+5FOA plates (25 repeat plasmids)or SC-His-Ura plates (50 repeat plasmids). The frequency of background mutation for each plasmid was calculated by dividing the number of colonies on selective media by the total number of transformants.

PCR analysis:

PCR analysis was performed to determine the percentage of colonies that had taken up a plasmid with a bona fide change in TNR size. Isolated colonies on SC-His+5FOA plates or SC-His-Ura plates were picked, and the cells disrupted in 100 $\mu$l of 50 mM dithiothreitol/0.5% Triton X-100, incubated at 37° C. for 30 minutes, heated at 95° C. for 5 minutes and kept on ice thereafter. A portion of this material was used as a template for PCR amplification as described previously (23), with the following modifications. Amplification was carried out for 30 cycles (30 seconds at 94° C., 30 seconds at 58° C. and 30 seconds at 72° C.), plus a final extension at 72° C. for 5 minutes in the presence of approximately 1.25 $\mu$Ci of [$\alpha$-$^{32}$P-dCTP]. The products were then separated on a 6% denaturing polyacrylamide gel. PCR product sizes (±2 repeat units) were determined by comparison with a DNA-sequencing ladder (M13 DNA). To determine the actual mutation frequencies, the frequencies calculated above (from the selective plates) were multiplied by the percentage of plasmids with bona fide alterations in TNR size.

Figure 2:
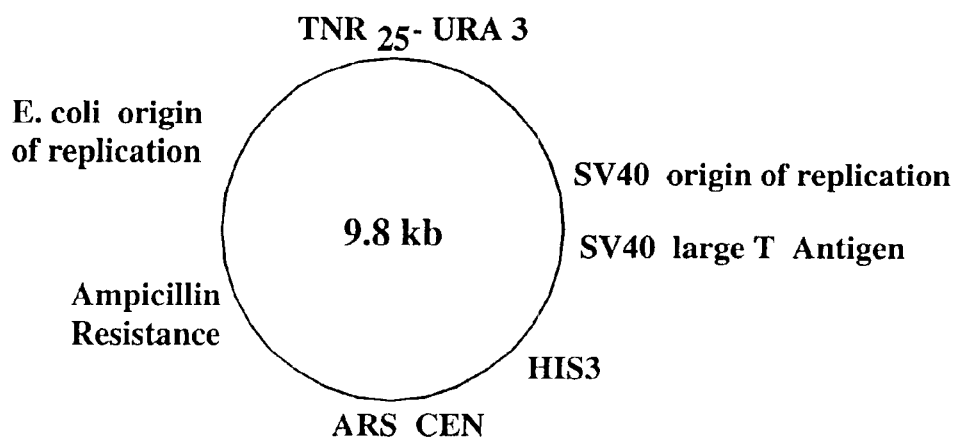
FIG. 2 is a diagram of the DNA shuttle vector for assessing TNR expansions. This DNA plasmid contains an SV40 origin of replication, the gene for SV40 large T antigen, a TNR-URA3 reporter gene encoding a TNR tract of 25 repeats, an *E. coli* origin of replication and an ampicillin resistance gene.

II. Results
  DNA Shuttle Vector:
  The essential features of an exemplary TNR expansion vector are shown in FIG. 2. This DNA plasmid contains an SV40 origin of replication which provides the means to replicate the vector in human and other mammalian cell types making this vector highly portable between different cell culture systems. Nucleic acid sequences encoding the SV40 large T antigen are also contained in the shuttle vector. In conjunction with the activities of large T antigen, host cell factors mediate replication from the SV40 origin present on the shuttle vector. The shuttle vector further comprises a TNR-URA3 reporter system which facilitates detection of TNR tract alterations. The shuttle vector also contains the yeast HIS3 gene, which is used to identify transformants (i.e., to select yeast cells that have taken up a plasmid); the yeast genetic element ARS (autonomously replicating sequence, i.e., an origin of DNA replication); and CEN, a centromere element that controls plasmid number in yeast to 1–2 copies per cell. For cloning and propagation purposes, the vector also contained an E. coli origin of replication and an ampicillin resistance gene. Thus, this DNA plasmid is a three-way shuttle vector, capable of replicating in mammalian cells, in yeast, and in E. coli.
  TNR Expansion Assay:
  The expansion assay developed in accordance with the present invention facilitates the selection of yeast cells harboring TNR tract expansions. The assay monitors expression of a reporter gene whose transcription depends upon the length of the TNR tract. First, a shuttle vector containing TNR sequences of approximately 25 repeats is transfected into human 293T cells. Cells may be transfected in a variety of ways including CaPo$_4$ precipitation, electroporation and lipofection. Those of ordinary skill in the art are familiar with such methods. 293T cells readily take up plasmid DNA, obviating the need to select for transfectants. Also, SV40-based plasmids exhibit very low mutation rates in HEK-derived cell lines (24). Thus, random inactivation of the reporter gene during incubation in these cells is very infrequent and a low baseline in the genetic assay is observed. Transfected 293T cells provide high yields of SV40-based plasmids (typically $10^4$ to $10^5$ copies per cell; 25). This copy number ensures a high yield of recovered plasmid from the transfected cells.
  Transfected 293T cells are cultivated for 2–3 days to provide sufficient time for replication of the transfected DNA. After cultivation, the transfected DNA is rescued from the cells using standard protocols (21), and then transfected into his3 ura3 yeast cells by CaPO$_4$ transfection procedures. Transfectants are identified by a His$^+$ phenotype (ability to grow without histidine in the media), due to the complementation of the chromosomal his3 allele with the wild type HIS3 gene present on the plasmid. A small fraction of the transfectants are also plated on media lacking histidine to determine the total number of transformed cells. Most of the cells are plated on media that not only lack histidine but also contain the cytotoxic drug, 5-fluoroorotic acid (5FOA). Cells harboring unexpanded TNR plasmids are killed by 5FOA, whereas those cells which are transformed by an expanded plasmid survive 5FOA treatment (23). This genetic selection, therefore, facilitates the quantitation of expanded plasmids derived from the human cells, based on the ratio of 5FOA resistant yeast out of the total transformed population. Further, this assay is very sensitive as expansion rates measured in yeast varied over five orders of magnitude (100,000×; 26).
  Existing methods are also used (27) to reduce background in the assay through the elimination of plasmid DNA that is not taken up by 293T cells or which is not replicated. Prior to transformation into yeast, a small fraction of the plasmid preparations rescued from the 293T cells are digested by the restriction enzyme, DpnI. This enzyme cleaves GATC sequences that are adenine methylated on both strands. Since the DNA used to perform the transfection originated from E. coli, it was methylated and hence sensitive to DpnI cleavage. In contrast, any plasmid that undergoes replication in the 293T cells will be hemi-methylated or unmethylated because mammalian cells do not harbor the GATC-specific adenine methylase. As a result, replicated DNA will be resistant to DpnI. In this way, plasmid molecules that undergo replication are greatly enriched. Appropriate controls to prove this point indicate that plasmid DNA recovered from 293T cells is >80% resistant to DpnI, whereas <5% of the DNA from E. coli is resistant. This methodology has long been used in the V(D)J recombination field and is known to effectively remove >99% of the unreplicated molecules (27).
  Table II shows the experimental results for three test plasmids. pBL92 contained the sequence (CAG)$_{25}$, a sequence that is genetically unstable and expands with detectable frequencies in yeast (23) and in human sperm (28). In the TNR expansion system, (CAG)$_{25}$ was also unstable. Expansion frequencies were observed at levels of $1 \times 10^{-3}$ to $3 \times 10^{-3}$. This level of mutation contrasted strikingly with the level of spontaneous mutations for most sequences, which are typically $10^{-10}$ per nucleotide per generation. TNR expansions of (CAG)$_{25}$ were, therefore, orders of magnitude higher than background, spontaneous mutations.

TABLE II

EXPANSION FREQUENCIES OF TNR TRACTS

| PLASMID | REPEAT SEQUENCE | MUTATION FREQUENCY | BACKGROUND FREQUENCY | RATIO |
|---|---|---|---|---|
| pBL92 | (CAG)$_{25}$ | 1 to 3 × 10$^{-3}$ | <3 × 10$^{-5}$ | 100 |
| pBL161 | (TAQ)$_{25}$ | <1.4 × 10$^{-4}$ | <2.9 × 10$^{-6}$ | ~50 |
| pBL14 | (C,T,G)$_{25}$ | <1.9 × 10$^{-4}$ | <5.6 × 10$^{-6}$ | ~30 |

Not only were CAG expansions frequent in this system, they also required that the CAG sequence repeat itself. As a control, the sequence (TAG)$_{25}$ was tested because this repeat is genetically stable in yeast (23) and in humans. After performing the assay, no detectable expansion of (TAG)$_{25}$ occurred. Nor was expansion observed for the "scrambled" (C,T,G)$_{25}$ control. The "scrambled" control (23), contained a randomized sequence of 25 C's, 25 T's and 25G's, to eliminate the repeating nature to this "scramble" TNR sequence. Note that the Mutation Frequency values in Table II were upper limits, defined by the experiment. The actual values may be substantially lower. Thus, it was concluded that the frequent expansions of (CAG)$_{25}$ occurred in a sequence-dependent and repeat-dependent manner.
  Other TNR sequences that are known to expand in human cells, such as, CTG, CCG and CGG, may be assessed using the assay method of the present invention.
  PCR analysis and control experiments:
  To test whether the 5FOA resistant yeast cells contained plasmids with bona fide expansions, PCR analysis across the TNR locus was performed. The primers used were oBL91 (coordinates–54 to –31 of pBL24; SEQ ID NO: 1) and oBL157 (complementary to coordinates 53-30 of URA3; SEQ ID NO: 2). True expansions showed a larger PCR fragment than the starting tract, due to the extra TNR repeats. Seven examples of bona fide expansions (out of 36

5FOA resistant isolates examined) were detected with the TNR expansion assay. The expanded alleles were 4–13 repeats larger than the starting tract. This size range is typical in human families affected with the polyglutamine class of TNR diseases (29). PCR analysis also showed some 5FOA resistant cells with unchanged TNR tracts. These are presumably due to inactivating mutations occurring spontaneously within the URA3 gene. These inactivating events were unavoidable, but they were easily distinguished by PCR analysis.

Another important control experiment was performed to determine the background level of expansions in the TNR expansion assay. Background expansions could occur spontaneously in *E. coli*, during propagation of the plasmid. Additionally, such expansions may occur in yeast immediately upon uptake into the yeast cell. (Since 5FOA kills yeast cells very rapidly (30), it is very unlikely that a plasmid could be replicated in yeast prior to expansion.) Fortunately, both of these background events were easily controlled for by a simple variation of the experimental procedure. The plasmid preparation was transformed directly into yeast cells, i.e., without passaging through the human cells. The background expansion frequency (Table II) was then determined for this direct transformation control which showed very low levels of 5FOA resistance ($10^{-6}$ to $10^{-5}$) PCR analysis of these rare resistant cells indicated no expansions occurred at the TNR locus. Thus, it was presumed that these plasmids had a low-level of spontaneous inactivating mutations within the URA3 gene.

EXAMPLE 2

TNR Contractions in Eukaryotic Cells

Figure 3:
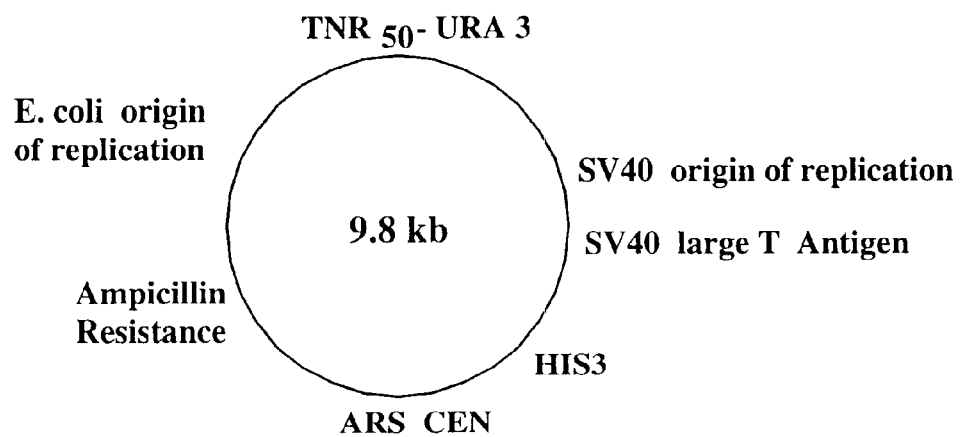
FIG. 3 is a diagram of the DNA shuttle vector for assessing TNR contractions. This vector is similar to that shown in FIG. 2, but contains a TNR tract of 33–50 repeats.

The TNR alteration assay may be adopted to monitor TNR contractions. FIG. 3 shows the simple variations in the shuttle vector necessary to measure TNR contractions. The shuttle vector used in the TNR contraction assay is assembled with a somewhat longer TNR tract, typically 33 or 50 repeats instead of the 25 repeats utilized in the expansion assay.

Detection of contractions involves a similar experimental approach as described for the determination of TNR expansions. The shuttle vector is first transfected in human 293T cells, recovered after 2–3 days, and then transfected into yeast cells. This approach provides a means to measure whether any contractions occur while the plasmid is replicating in the human 293T cells. Contractions of the TNR are readily monitored in yeast as the TNR of extended length prevents growth of cells without uracil when the URA3 gene is too far from its promoter to be expressed. TNR contractions that generate final tract lengths of 2–28 repeats in the human cells restore the expression of the URA3 gene, and yeast cells which take up plasmids with TNR contractions will grow on media without added uracil. Thus, this reporter system may be used to assay the percentage of plasmid molecules that confer a Ura$^+$ phenotype (growth without added uracil) to yeast cells. Contractions that occur during replication in human cells are identified as Ura$^+$ yeast transformants. PCR analysis and background checks will are then performed as described above to confirm bona fide contractions in the TNR repeat tracts.

The TNR mutability assay of the present invention is advantageous because it provides a genetic method to measure TNR instability in eukaryotic cells. This assay is sensitive, quantitative and experimentally tractable. This novel approach for measuring TNR instability in human and or other mammalian cells will greatly enhance the study of the genetic mechanisms associated with cancer and such genetic disorders as Fragile X syndrome, Huntington's disease and myotonic dystrophy.

REFERENCES

1. Ashley Jr., C. T. and S. T. Warren. (1995) Trinucleotide repeat expansion and human disease. Annu. Rev. Genetics 29, 703–728.

2. Gusella, J. F. and M. E. MacDonald. (1996) Trinucleotide instability: a repeating theme in human inherited disorders. Annu. Rev. Med. 47, 201–209.

3. Paulson, H. L. and K. H. Fischbeck. (1996) Trinucleotide repeats in neurogenetic disorders. Annu. Rev. Neurosci. 19, 79–107.

4. The Huntington's Disease Collaborative Research Group. (1993) A novel gene containing a trinucleotide repeat that is expanded and unstable on Huntington's disease chromosomes. Cell 72, 971–983.

5. Kremer, B., et al. (1994) A worldwide study of the Huntington's disease mutation: the sensitivity and specificity of measuring CAG repeats. New Eng. J. Med. 330, 1401–1406.

6. Mangiarini, L., et al. (1996) Exon 1 of the HD gene with an expanded CAG repeat is sufficient to cause a progressive neurological phenotype in transgenic mice. Cell 87, 493–506.

7. Telenius, H., et al. (1994) Somatic and gonadal mosaicism of the Huntington disease gene CAG repeat in brain and sperm. Nature Genetics 6, 409–414.

8. Goldberg, Y. P., et al. (1993) Molecular analysis of new mutations for Huntington's disease: intermediate alleles and sex of origin effects. Nature Genetics 5, 174–179.

9. Campuzano, V., et al. (1996) Friedreich's ataxia: autosomal recessive disease caused by an intronic GAA triplet repeat expansion. Science 271, 1423–1427.

10. Brook, J. D., et al. (1992) Molecular basis of myotonic dystrophy: expansion of a trinucleotide (CTG) repeat at the 3' end of a transcript encoding a protein kinase family member. Cell 68, 799–808.

11. Giovannucci, E., et al. (1997) The CAG repeat within the androgren receptor gene and its relationship to prostate cancer. Proc. Natl. Acad. Sci. 94, 3320–3323.

12. La Spada, A. R., E. M. Wilson, D. B. Lubahn, E. E. Harding, and K. H. Fischbeck. (1991) Androgen receptor gene mutations in X-linked spinal and bulbal muscular atrophy. Nature 352, 77–79.

13. Schoenberg, M. P., et al. (1994) Microsatellite mutation (CAG24AE18) in the androgen receptor gene in human prostate cancer. Biochem. Biophys. Res. Comm. 198, 74–80.

14. Chamberlain, N. L., E. D. Driver, and R. L. Miesfeld. (1994) The length and location of CAG trinucleotide repeats in the androgen receptor N-terminal domain affect transactivation function. Nucleic Acids Res 22, 3181–3186.

15. King, B. L., H.-Q. Peng, P. Goss, S. Huan, D. Bronson, B. M. Kacinski, and D. Hogg. (1997) Repeat expansion detection of (CAG)n tracts in tumor cell lines, testicular tumors and testicular cancer families. Cancer Res. 57, 209–214.

16. Burright, E. N., et al. (1995) SCA1 transgenic mice: a model for neurodegeneration caused by an expanded CAG trinucleotide repeat. Cell 82, 937–948.

17. Gourdon, G., et al. (1997) Moderate intergenerational and somatic instability of a 55-CTG repeat in transgenic mice. Nature Genet. 15, 190–192.

18. Monckton, D. G., M. I. Coolbaugh, K. T. Ashizawa, M. J. Siciliano, and C. T. Caskey. (1997) Hypermutable myotonic dystrophy CTG repeats in transgenic mice. Nature Genet. 15, 193–196.

19. Mangiarini, L., K. Sathasivam, A. Mahal, R. Mott, M. Seller, and G.P. Bates. (1997) Instability of highly expanded CAG repeats in mice transgenic for the Huntington's disease mutation. Nature Genet. 15, 197–200.

20. Graham, F. L., and Van Der Eb, A. J. (1973). A new technique for the assay of infectivity of human adenovirus 5 DNA. Virology 52, 456–467.

21. Hirt, B. (1967). Selective extraction of polyoma DNA from infected mouse cell cultures. J. Mol. Biol. 26, 365–369.

22. Maniatis, T., Fritsch, E. F., and Sambrook, J. (1989). Molecular cloning: a laboratory manual (New York: Cold Spring Harbor Laboratory).

23. Miret, J. J., Pessoa-Brandao, L., and Lahue, R. S. (1998). Orientation-dependent and sequence-specific expansions of CTG/CAG trinucleotide repeats in *Saccharomyces cerevisiae*. Proc. Natl. Acad. Sci. 95, 12438–12443.

24. Hsia, H. C., Lekowski, J. S., Leong, P.-M., Calos, M. P., and Miller, J. H. (1989). Comparison of ultraviolet irradiation-induced mutagenesis of the lacI gene in *Escherichia coli* and in human 293 cells. J. Mol. Biol. 205, 103–113.

25. DuBridge, R. B., and Calos, M. P. (1988). Recombinant shuttle vectors for the study of mutagenesis. Mutagenesis 3, 1–9.

26. Spiro, C., Pelletier, R., Rolfsmeier, M. L., Dixon, M. J., Lahue, R. S., Gupta, G., Park, M. S., Chen, X., Mariappan, S. V. S., and McMurray, C. T. (1999). Inhibition of FEN-1 processing by DNA secondary structure at trinucleotide repeats. Molec. Cell 4, 1079–1085.

27. Lieber, M. R., Hesse, J. E., Mizuuchi, K., and Gellert, K. (1987). Developmental stage specificity of the lymphoid V(D)J recombination activity. Genes Dev. 1, 751–761.

28. Leeflang, E. P., Tavare, S., Marjoram, P., Neal, C. O. S., Srinidhi, J., MacDonald, M. E., deyoung, M., Wexler, N. S., Gusella, J. F., and Arnheim, N. (1999). Analysis of germline mutation spectra at the Huntington's disease locus supports a mitotic mutation mechanism. Hum. Mol. Genet. 8, 173–183.

29. Paulson, H. L., and Fischbeck, K. H. (1996). Trinucleotide repeats in neurogenetic disorders. Annu. Rev. Neurosci. 19, 79–107.

30. Boeke, J. D., Lacroute, F., and Fink, G. R. (1984). A positive selection for mutants lacking orotidine-5'-phosphate decarboxylase activity in yeast: 5-fluoroorotic acid resistance. Mol. Gen. Genet. 197, 345–346.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting alterations in trinucleotide repeat tract lengths, comprising the steps of:
   a) contacting mammalian cells with a shuttle vector containing a trinucleotide repeat tract under conditions whereby said shuttle vector enters and replicates in said mammalian cells;
   b) recovering the replicated shuttle vector from said mammalian cells;
   c) introducing the recovered shuttle vector into a yeast cell in the presence of a selection agent, alteration of the trinucleotide repeat tract length conferring resistance to said selective agent; and
   d) selecting yeast cells comprising the shuttle vector DNA containing trinucleotide repeat tract length alterations which survive in the presence of said selection agent.

2. The method of claim 1, comprising the additional steps of:
   e) recovering the shuttle vector containing trinucleotide repeat tract length alterations from the yeast cells which survive in the presence of said selection agent; and
   f) analyzing the recovered shuttle vector to identify the trinucleotide repeat tract length alterations.

3. The method of claim 1, wherein said mammalian cells are selected from the group consisting of 293T cells, LoVo cells, HCT116 cells, DLD1 cells, XP-A cells, XP-B cells, cancer cells, normal primary cells, neuronal cells, tumor cells, muscle cells, hepatocytes, myocytes, fibroblasts and cells from individuals afflicted with a trinucleotide repeat-associated disorder.

4. The method of claim 1, wherein said yeast cells are selected from the group consisting of Saccharomyces cerevisiae cells and Saccharomyces pombe cells.

5. The method of claim 2, wherein the recovered shuttle vector DNA is analyzed by a method selected from the group consisting of polymerase chain reaction, nucleotide sequencing and gel electrophoresis.

6. The method of claim 1, wherein the shuttle vector DNA comprises a trinucleotide repeat tract having trinucleotides selected from the group consisting of: CAG, GTG, CCG, CGG, GAA, TAG, and scrambled C, T, G.

7. The method of claim 6, wherein the trinucleotide repeat tract is operably linked to a reporter molecule.

8. The method of claim 7, wherein the shuttle vector DNA further comprises an SV40 origin of replication, a yeast HIS3 gene, yeast autonomous replication sequence elements, a centromere element, an *E. coli* origin of replication and at least one sequence encoding a selectable marker.

9. The method of claim 2, wherein said trinucleotide repeat tract is isolated from a trinucleotide repeat instability gene selected from the group consisting of FMR1, FMR2, X25, DMPK, SCA8, SCA12, AR, HD, DRPLA, SCA1, SCA2, SCA3, SCA6 and SCA7.

10. The method of claim 9, wherein the isolated trinucleotide repeat tract is operably linked to a yeast URA3 gene.

11. The method of claim 9, wherein said trinucleotide repeat tract optionally comprises between 5 and 200 flanking nucleotides from said trinucleotide repeat instability gene.

12. The method of claim 1, wherein the shuttle vector DNA contains an initial trinucleotide repeat tract length of 25 repeats for assessing expansions in the trinucleotide repeat tract length.

13. The method of claim 1, wherein said yeast cells containing trinucleotide repeat tract length alterations survive on media lacking histidine and containing 5-fluoroorotic acid.

14. The method of claim 1, wherein the shuttle vector DNA contains an initial trinucleotide repeat tract length of approximately 33 repeats for assessing contractions in the trinucleotide repeat tract length.

15. The method of claim 1, wherein the shuttle vector DNA contains an initial trinucleotide repeat tract length of approximately 50 repeats for assessing contractions in the trinucleotide repeat tract length.

16. The method of claim 1, wherein the yeast cells containing trinucleotide repeat tract length alterations survive on media lacking uracil and containing 5-fluoroorotic acid.

17. A method for identifying trinucleotide repeat tract length expansions, comprising the steps of:
  a) contacting mammalian cells with a shuttle vector containing a trinucleotide repeat tract of approximately 25 repeats under conditions whereby said shuttle vector enters and replicates in said mammalian cells;
  b) recovering the replicated shuttle vector from said mammalian cells;
  c) introducing the recovered shuttle vector into a yeast cell in the absence of histidine, expansion of the trinucleotide repeat tract length conferring a His+ phenotype; and
  d) selecting yeast cells comprising the shuttle vector containing trinucleotide repeat tract length expansions which survive in the absence of histidine.

18. The method of claim 17, further comprising:
  e) recovering the shuttle vector from the yeast cells which survive in the absence of histidine; and
  f) analyzing the recovered shuttle vector to identify the trinucleotide repeat tract length expansions.

19. A method for identifying contractions in trinucleotide repeat tract lengths, comprising the steps of:
  a) contacting mammalian cells with a shuttle vector containing a trinucleotide repeat tract of approximately 33 repeats under conditions whereby said shuttle vector enters and replicates in said mammalian cells;
  b) recovering the replicated shuttle vector from said mammalian cells;
  c) introducing the recovered shuttle vector into a yeast cell in the absence of uracil, contraction of said trinucleotide repeat tract length conferring a Ura+ phenotype; and
  d) selecting yeast cells comprising the shuttle vector containing trinucleotide repeat tract length contractions which survive in the absence of uracil.

20. The method of claim 19, further comprising:
  e) recovering the shuttle vector from the yeast cells which survive in the absence of uracil; and
  f) analyzing the recovered shuttle vector to identify the trinucleotide repeat tract length contractions.

21. A method for identifying contractions in trinucleotide repeat tract lengths, comprising the steps of:
  a) contacting mammalian cells with a shuttle vector containing a trinucleotide repeat tract of approximately 50 repeats under conditions whereby said shuttle vector enters and replicates in said mammalian cells;
  b) recovering the replicated shuttle vector from said mammalian cells;
  c) introducing the recovered shuttle vector into a yeast cell in the absence of uracil, contraction of said trinucleotide repeat tract length conferring a Ura+ phenotype; and
  d) selecting yeast cells comprising the shuttle vector containing the trinucleotide repeat tract length contractions which survive in the absence of uracil.

22. The method of claim 21, further comprising:
  e) recovering the shuttle vector from the yeast cells which survive in the absence of uracil; and
  f) analyzing the recovered shuttle vector to identify the trinucleotide repeat tract length contractions.

* * * * *